United States Patent [19]

Karamian

[11] 4,342,915
[45] Aug. 3, 1982

[54] APPARATUS FOR PREVENTING BACTERIAL PASSAGE INTO STERILE FLUID SYSTEMS

[76] Inventor: Narbik A. Karamian, 7609 Exeter Rd., Bethesda, Md. 20014

[21] Appl. No.: 233,322

[22] Filed: Feb. 11, 1981

Related U.S. Application Data

[63] Continuation-in-part of Ser. No. 926,664, Jul. 21, 1978, Pat. No. 4,276,256, which is a continuation-in-part of Ser. No. 737,740, Nov. 1, 1976, abandoned.

[51] Int. Cl.³ .............................................. A61L 2/10
[52] U.S. Cl. ................................... 250/436; 137/237; 250/432 R; 422/24
[58] Field of Search ........................... 250/432 R, 436; 137/237; 422/24

[56] References Cited

U.S. PATENT DOCUMENTS

| | | | |
|---|---|---|---|
| 2,338,387 | 1/1944 | Whitman | 250/436 |
| 2,381,031 | 8/1945 | Blushfield | 137/241 |
| 2,537,774 | 1/1951 | Machinist | 210/764 X |
| 3,433,946 | 3/1969 | Hardwick | 422/24 X |
| 3,589,862 | 6/1971 | Veloz | 422/24 X |

Primary Examiner—Barry S. Richman
Attorney, Agent, or Firm—Joseph P. Nigon

[57] ABSTRACT

An apparatus for preventing microorganisms from passing from outside into sterile closed systems containing sterile water or other fluids for general or biomedical use.

3 Claims, 4 Drawing Figures

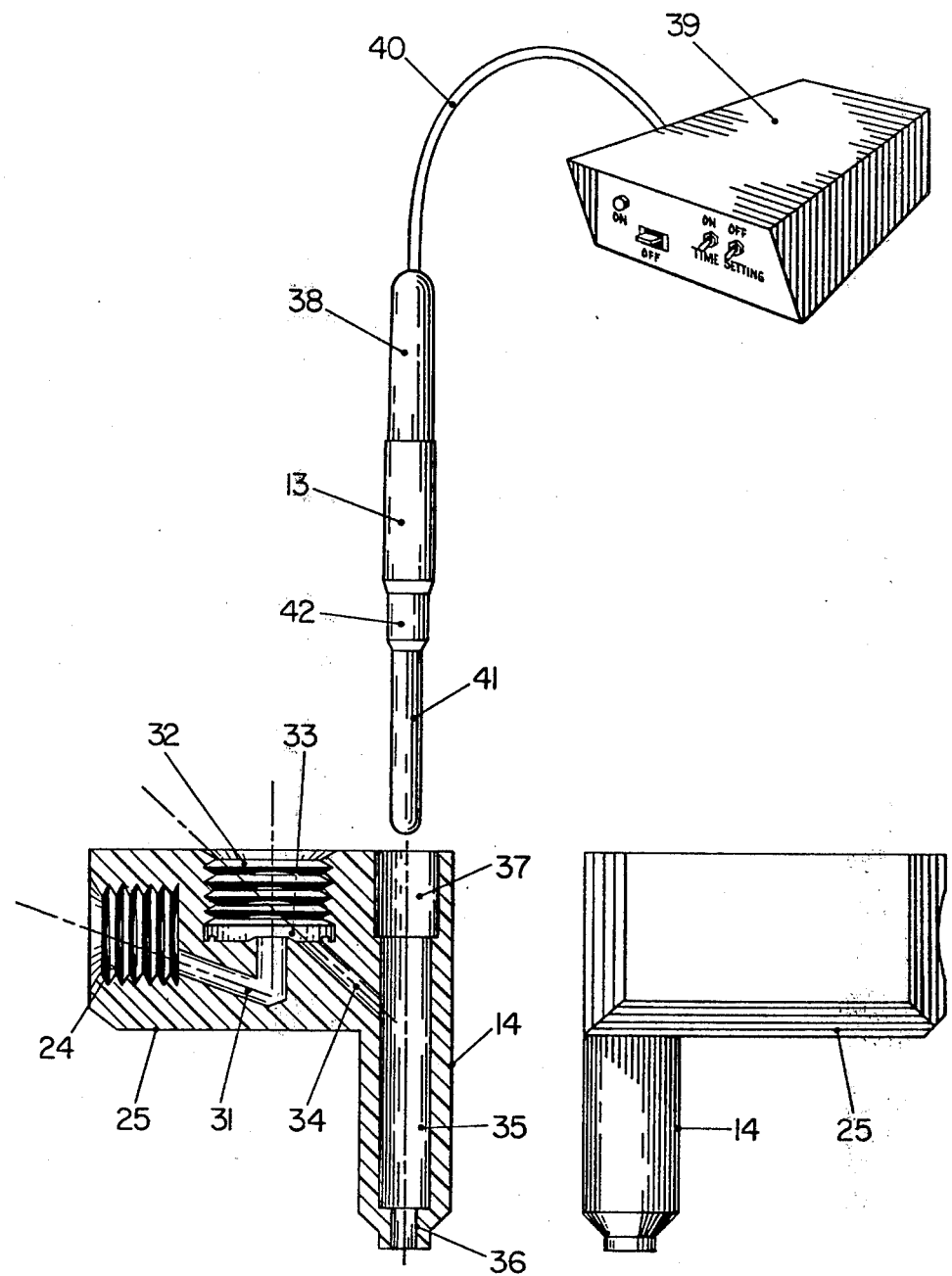

APPARATUS FOR PREVENTING BACTERIAL PASSAGE INTO STERILE FLUID SYSTEMS

CROSS REFERENCE TO OTHER APPLICATIONS

This application is a continuation in part of application Ser. No. 926664 filed July 21, 1978, now U.S. Pat. No. 4,276,256 issued June 30, 1981, which is in turn a continuation in part of application Ser. No. 737,740 filed Nov. 1, 1976 and now abandoned.

FIELD OF THE INVENTION

The invention relates to an apparatus for preventing microorganism contamination from outside environment into water or other fluids that have been previously sterilized to assure that they are microorganism free. The fluids drawn off through this apparatus either continuously or intermittently will remain microorganism free even after substantial outside surface bacterial contamination of the apparatus. This contamination may arise from handling and/or from environmental factors.

BACKGROUND OF THE INVENTION

There has been a constant demand for high purity bacteria and endotoxin free water for research and intravenous admixtures. U.S. Pat. No. 4,089,749 describes an apparatus for preparing such water. The references cited in this application disclose prior art systems for preparing high purity bacteria and endotoxin free water.

Very briefly this patent describes an apparatus for the continuous production of high-purity water including a distillation flask, a carboy and a condenser unit. A filter is provided between the atmosphere and the interiors of the flask, the carboy and the condenser unit to remove airborne bacteria from entering the apparatus. The open parts are interconnected with inert flexible tubing pieces. A two-way stopcock allows high purity water to be removed from the carboy.

It has been found that although the apparatus for producing high-purity water described in U.S. Pat. No. 4,089,749 produces a high quality product, there is a possibility of bacterial contamination of the product being stored in the carboy system from outside through the ordinary two way faucet being used for drawing off the water. The bacteria, generally are either airborne or grow on human skin and transfer on to the valve during handling.

Various devices have been proposed for preparing sterile liquids. U.S. Pat. No. 2,456,152 describes a device wherein the outlet faucet is continuously bathed in steam. U.S. Pat. No. 2,537,774 relates to a device that utilizes ultraviolet radiation to sterilize liquids. French patent 1,101,643 uses a combination of ultraviolet and infrared radiation to prepare sterile liquids.

In all of these devices either the liquid being withdrawn is heated to a temperature substantially above room temperature, or there is no provision for preventing bacterial contamination from outside sources.

SUMMARY OF THE INVENTION

It is the principal object of the invention to provide an apparatus for preventing bacterial contamination of water or other liquids that have been previously treated to assure that they are sterile without increasing the temperature of the liquid being withdrawn.

It is another object of the present invention to provide a continuous source of high purity, bacteria free water or other fluids by assuring that sources of this water or fluids are not recontaminated through bacterial accumulation on the valves or faucets connected to the system.

BRIEF DESCRIPTION OF THE DRAWINGS

FIG. 2 is a front perspective view of the lower portion of the faucet of FIG. 1.

FIG. 3 is a cross sectional view of the lower portion of the faucet of FIG. 1, also showing details of the light source.

DETAILED DESCRIPTION OF THE PREFERRED EMBODIMENTS

Figure 1:
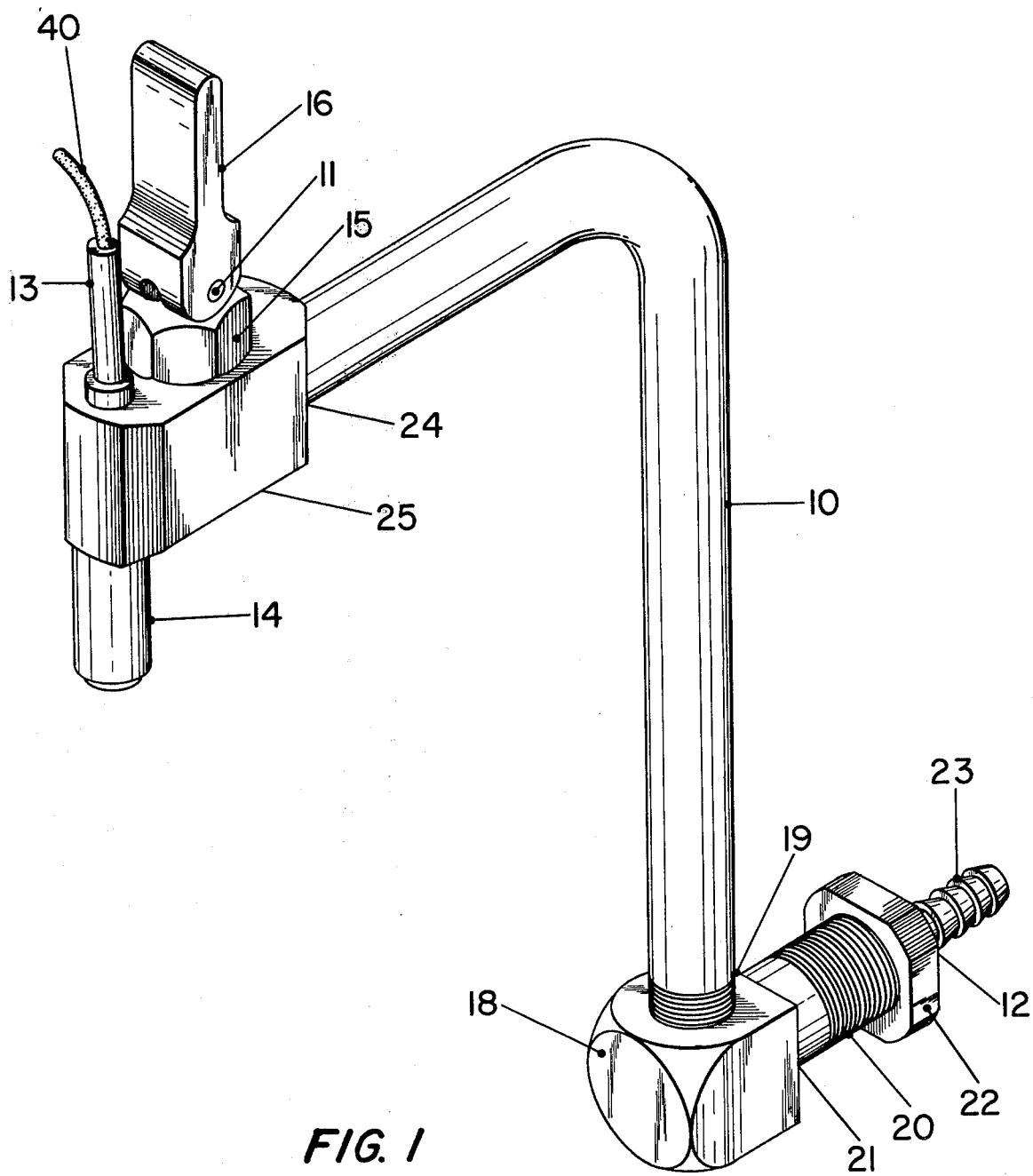
FIG. 1 is a front perspective view of the preferred embodiment of the invention.

Referring now to FIG. 1 which shows a faucet attached to a conduit 10 designed to be readily attached to and detached from a source of sterile water (not shown). An elbow 18 is threadably attached to one end of the conduit 10 at 19. A short conduit 20 is attached to an elbow 18 at the joint 21. A nipple 12 having corrugations 23 thereon for ease of attachment to a rubber or plastic tubing is threadably attached to the conduit 20. A lock nut 22 secures the faucet if it is attached to a support.

The other end 24 of the conduit 10 is threadably attached to the faucet structure 25. The faucet per se is commercially available and is not part of the invention. The faucet 25 includes a toggle member 15 threadably attached to a handle 16. The handle 16 moves from the open to the closed position about a pin 11 to open and close the faucet. The invention resides in the modification of this commercially available faucet to include an ultra violet source 13 attached by wire 40 to a control unit (not shown). The ultra violet source 13 is positioned in a spout 14 and maintains the spout 14 free of bacterial contamination. The water passing through the faucet 25 may also be contacted by ultra violet radiation. The water passing through the spout 14 is thus sterile at all times.

Referring now to FIGS. 2 and 3 which show the details of the faucet structure and the essential features of the invention.

The faucet 25 is shown in cross section and consists of a threaded portion 24 designed to be attached to the conduit 10 leading to a conduit 31, which leads to a water receiving chamber 32. A diaphram is positioned in the seat 33 and is moved from the open to the closed position by movement of the handle 16 shown in FIG. 1. A conduit 34 connects the chamber 32 to the channel 35 in the spout 14. The channel 35 has a narrow area at 36 and an enlarged area at 37.

The light source 13 has an upper portion 38 that contains electrodes (not shown) attached to a control unit 39 by means of a wire 40. The lower portion of the light source 13 consists of a quartz tube 41 filled with mercury vapor. A plastic collar 42 is machined to fit into the elarged area 37 of the spout 14.

Figure 4:
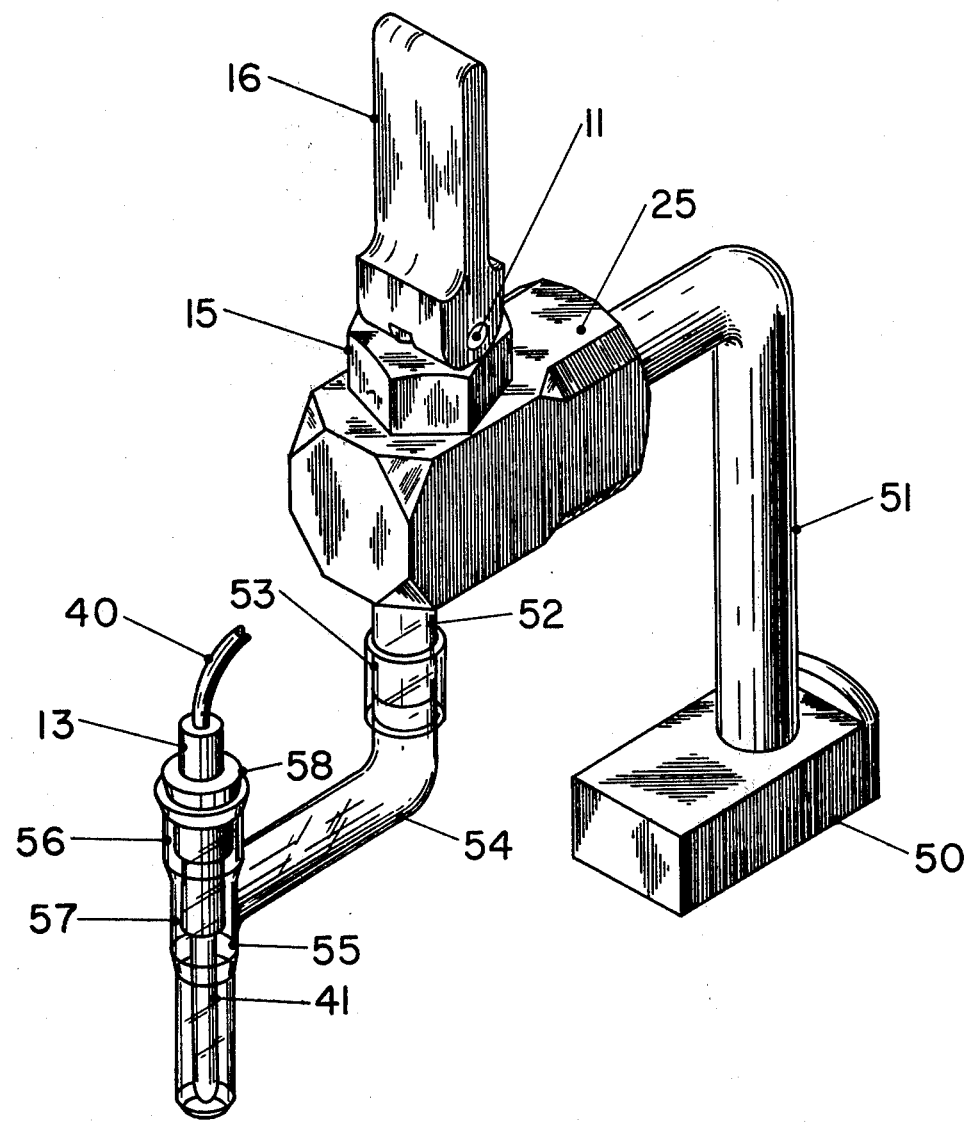
FIG. 4 shows another embodiment of the invention.

FIG. 4 shows another embodiment of the invention. In this embodiment the base 50 is attached to a conduit 51 and extends to the toggle valve member 25 described in detail with reference to FIGS. 1 and 3. A spout 52 is detachable connected by means of a collar 53 to the L shaped conduit 54. The forward end of the conduit 54 terminates in a conduit 55. The conduit 55 has an enlarged portion 56, and a restricted portion 57. An ultra violet source 13 is inserted in a stopper 58. The ultra violet source 13 contains electrodes (not shown) attached by means of the wire 40, to a control (not shown). The lower portion of the ultra violet slight source 13 consists of a quartz tube 41 filled with mercury vapor.

In operation of the device the ultra violet lamp 13 is positioned in the faucet 25 as shown in the figures. Water passes thru the conduit 10 into the faucet 25. The faucet handle 16 moves the toggle member 15 to move the diaphram 33 of FIG. 3 so that water can flow thru the conduits 31 and 34 into the conduit 35. The ultra violet light source is energized by the control unit 39 and emits ultra violet light thru the quartz tube 41 positioned in the conduit 35 in FIG. 3. The water in conduit 35 (in FIG. 3) is protected by the ultra violet light. The control unit 39 controls the time the ultra violet light is energized. The ultra violet light is energized periodically for short periods of time to prevent contamination of the spout 14 from outside sources.

In operation of the device shown in FIG. 4, the fluid moves through the conduit 51 and into the valve 25. When the valve is opened water moves through conduits 52 and 54 into the conduit 55. This conduit 55 is maintained in a sterile condition by intermittent operation of the ultra violet light 13.

What is claimed is:

1. An apparatus for preventing bacterial passage into a sterile fluid which comprises in combination a source of sterile fluid, a conduit attached to said source of sterile fluid, a fluid delivery faucet including a shut-off valve means attached to said conduit, said faucet having a delivery spout attached thereto and downstream therefrom, including a substantially unrestricted annular sterile fluid flow path therein, said delivery spout having an ultraviolet light positioned in the center thereof, means for periodically energizing said ultraviolet light so that the annular flow path defined by the exterior of the ultraviolet light and the interior of the delivery spout is irradiated with ultraviolet light to assure bacterial sterility.

2. The apparatus according to claim 1 wherein the source of ultraviolet light is a quartz tube with mercury vapor with a pair of electrodes connected to a source of electricity.

3. An apparatus for preventing bacterial contamination of sterile water comprising in combination:
   (a) a faucet designed to be attached to a supply of sterile distilled water, said faucet having a hollow casing with a water receiving chamber, said casing having an outlet spout member communicating with said chamber, and also having an inlet element also communicating with said chamber, said inlet element embodying a threaded section for receiving a conduit for connection to said supply of sterile distilled water, and said faucet having means for selectively closing the inlet against the direction of flow,
   (b) said outlet spout having an enlarged tubular portion positioned above a smaller tubular portion, an ultraviolet source positioned in said enlarged portion, said ultraviolet source consisting of a quartz tube filled with mercury vapor, said quartz tube extending from said enlarged portion into said smaller tubular portion, a pair of electrodes operably connected to said mercury vapor within said quartz tube, said electrodes being positioned in a plastic collar means and being connected to an energized control unit, said collar means dimensioned to fit snugly into the enlarged tubular portion in said outlet spout thereby suspending said quartz tube in the center of said smaller tubular portion of said spout and defining therewith a substantially unrestricted annular flow path for delivery of said sterile fluid.

* * * * *